United States Patent [19]

Miyazaki et al.

[11] Patent Number: 5,308,849
[45] Date of Patent: May 3, 1994

[54] METHOD OF REDUCING ELEVATED INTRAOCULAR PRESSURE

[75] Inventors: Hirohisa Miyazaki, Wakayama; Hitoshi Tanaka, Nara; Katsuhiko Morisaki, Yamatokoriyama, all of Japan

[73] Assignee: Rohto Pharmaceutical Co., Ltd., Osaka, Japan

[21] Appl. No.: 55,014

[22] Filed: Apr. 30, 1993

[30] Foreign Application Priority Data

Dec. 3, 1992 [JP] Japan ................... 4-324126

[51] Int. Cl.$^5$ ............................. A61K 31/44
[52] U.S. Cl. ........................ 514/279; 514/913
[58] Field of Search ................ 514/285, 279, 913

*Primary Examiner*—Zohreh A. Fay
*Attorney, Agent, or Firm*—Venable, Baetjer, Howard & Civiletti

[57] ABSTRACT

A method of reducing elevated intraocular pressure which comprises administering the compound of the formula (1):

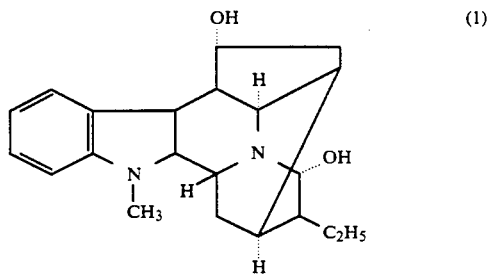

or a pharmaceutically acceptable salt thereof to patients suffering from abnormally elevated intraocular pressure is provided. A pharmaceutical formulation containing the compound of the formula (1) as an essential component is also provided.

2 Claims, No Drawings

METHOD OF REDUCING ELEVATED INTRAOCULAR PRESSURE

The present invention relates to a novel agent which is useful for the treatment of ocular hypertension (elevated intraocular pressure), and glaucoma. More specifically, this invention relates to a pharmaceutical composition for reducing elevated intraocular pressure which comprises as an essential component ajmaline of the following formula (1) or any one of pharmaceutically acceptable salts thereof.

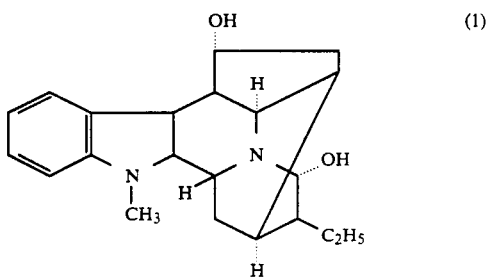

(1)

The present invention also relates to a method of reducing elevated intraocular pressure, which comprises administering the compound (1) to patients suffering from abnormally elevated intraocular pressure.

Glaucoma is a disease in which the intraocular pressure (IOP) is persistently or recurrently elevated above the normal range of pressure, which gives organic damage to ocular structures and further impairment of visual function which leads to, for instance, reduction of visual field. "Ocular hypertension" herein used is the term coined to denote an elevated intraocular pressure above the normal level, which is not accompanied by any functional impairment of vision, but, after a long period of time, may develop glaucoma. The medical treatment of ocular hypertension or glaucoma is directed to the reduction of the elevated intraocular pressure down to the normal IOP that induces no functional impairment, and also directed to the maintenance of the normal IOP.

In the present specification, an agent which is useful for reducing elevated intraocular pressure which is found in the ocular hypertension and glaucoma may sometimes be referred to as "antiglaucoma agent" for simplicity.

Conventional antiglaucoma agents known to be effective in the treatment of ocular hypertension or glaucoma are: carbonic anhydrase inhibitors (oral administration), hyperosmotic agents (injection), pilocarpine, epinephrine and its prodrug dipivefrine (eye drops). More recently, β-blockers (eye drops) are being extensively used for this purpose. However, all these agents have many disadvantages. Carbonic anhydrase inhibitors, for example, are known to have side effects such as gastrointestinal disturbances and general malaise and, in long-term therapy, may induce renal stone formation. Hyperosmotic agents are used mainly in the treatment of acute attacks due to postoperative sudden rise in IOP and are not appropriate for the long-term therapy for glaucoma or ocular hypertension.

Pilocarpine eye drops are known to have several side effects such as feeling of obfuscation due to miosis-induced arctation of the visual field and accommodation disorders due to contraction of the ciliary muscle. Epinephrine and dipivefrine eye drops induce conjunctival congestion, ophthalmalgia and tachycardia. The eye drops containing β-blockers as an active ingredient have been reported to cause systemic side effects such as headache and depression through their CNS (central nervous system) action, asthmatic symptoms by acting on the respiratory system and bradycardia and hypotension through its cardiovascular action (Iyaku Journal (Medicine and Drug Journal) 28: 705, 1992). When applied topically, β-blockers produce a feeling of dryness due to reduced lacrimal fluid and irritation at the time of instillation. These β-blockers are disadvantageous in that they are contraindicated for patients with bradycardia or bronchial asthma because the above side effects are particularly augmented in these patients (American Journal of Ophthalmology 102: 606, 1986). As described above, none of these antiglaucoma agents now in widespread use are satisfactory.

It is one objective of this invention to provide a novel antiglaucoma agent for treating ocular hypertension or glaucoma, which agent possesses an excellent ocular hypotensive effect (i.e., intraocular pressure-reducing effect) and no significant side effects, in particular, a minimal eye irritating effect.

As a result of extensive study seeking for excellent antiglaucoma agents, the present inventors have found that the compound (1) known as an antiarrhythmic agent has an ocular hypotensive effect, an effect unpredicted from the known major pharmacological effects, and minimal eye irritating effect, and therefore, the compound (1) is useful for the treatment of ocular hypertension or glaucoma. This pressure-reducing effect of the compound (1) was discovered by the present inventors in the first place.

The pharmacological properties of the compound (1) suggest that the compound (1) has no side effects such as miosis and accommodation disorders found in pilocarpine eye drops or conjunctival congestion found in epinephrine and dipivefrine eye drops. Compound (1) has also been reported to have no effect on respiration or blood pressure (The 12th Edition of Explanation of Japanese Pharmacopoeia, C-29, 1991) and is therefore considered to be free of any systemic hypotensive effect or adverse effects on the respiratory system associated with β-blockers (eye drops). Accordingly, the compound (1) is a highly useful agent for the treatment of ocular hypertension or glaucoma without having significant side effects possessed by conventional agents.

Compound (1) is described in Japanese Pharmacopoeia, and it can be synthesized by referring, for example, to the published literatures listed under "184. Ajmaline" on page 33 in the 11th Edition of Merck Index. A commercially available compound (1) can also be used (SIGMA CHEMICAL COMPANY).

Examples of pharmaceutically acceptable salts of the compound (1), which can be the antiglaucoma agent of the present invention, are those formed with inorganic and organic acids, such as hydrochloride, sulfate, nitrate, phosphate, hydrobromate, tartrate, acetate, citrate, fumarate, maleate and oxalate.

The antiglaucoma agent of the present invention can be formulated in a pharmaceutical composition having an appropriate unit dosage form by mixing the compound of the formula (1) or a pharmaceutically acceptable salt thereof with conventional vehicles for pharmaceutical use. The unit dosage form can be any one of conventional dosage forms. Examples of the dosage forms for topical administration may be eye drops and eye ointments, and those for systemic administration may be tablets, granules and injections. It is particularly desirous to use the antiglaucoma agent of the present invention in the form of eye drops.

When used as an eye drop, it is desirous to prepare the formulation which contains the compound (1) at a concentration ranging from 0.001 to 0.5%. Additives that are usually used in formulating eye drops can be used together with the compound (1). Additives to be used include preservatives such as chlorobutanol, sodium dehydroacetate, benzalkonium chloride, cetylpyridinium chloride, phenethyl alcohol, methyl paraoxybenzoate and benzethonium chloride, buffering agents such as borax, boric acid and potassium dihydrogen phosphate, viscosity-increasing agents such as methylcellulose, hydroxyethylcellulose, carboxymethylcellulose, hydroxypropyl methylcellulose, polyvinyl alcohol, sodium carboxymethylcellulose and chondroitin sulfate, solubilizing agents such as polysorbate 80 and polyoxyethylene hydrogenated castor oil 60, and stabilizers such as disodium edetate and sodium bisulfite. It is desirous that eye drops are isotonic with lacrimal fluid, and, for this reason, isotonicating agents such as sodium chloride, potassium chloride, and glycerin may be added as necessary. The pH of the formulation may be at any point within an ophthalmologically acceptable range and is preferably between pH 5.0 and pH 8.0.

The dosage and administration mode of the eye drops of the present invention can vary depending on patients' conditions and age. The usual single dosage, however, is 1-5 drops and administered two to four times daily. For ophthalmic ointments, an appropriate amount is placed in the conjunctival sac one to three times daily.

In the accompanying drawings:

FIG. 1 shows the test results on the major pharmacology (ocular hypotensive effect) of the eye drops of the present invention.

FIG. 2 shows the test results of the eye irritation test on the eye drops of the present invention.

The present invention is explained in more detail below by examples and experiments, but this invention is not limited to these examples and experiments.

In these examples, ajmaline of the formula (1) was used as compound (1).

EXAMPLE 1

| Formulation 1: | |
|---|---|
| Ingredients | Amount per 100 ml |
| Compound (1) | 500 mg |
| Glycerin | 2280 mg |
| Benzalkonium chloride | 10 mg |
| 1N hydrochloric acid | appropriate amount |
| 0.01N sodium hydroxide | appropriate amount |
| Sterile distilled water | appropriate amount |
| pH 7.0 | |

Production

Compound (1) is suspended in 90 ml of sterile distilled water and dropwise added with 1N hydrochloric acid while stirring to effect dissolution. To the resultant solution, glycerin, benzalkonium chloride and 0.01N sodium hydroxide were added, and sterile distilled water was added to the resultant solution to make 100 ml.

EXAMPLE 2

Another eye drop (Formulation 2) was prepared according to the same procedure described in Example 1.

| Formulation 2: | |
|---|---|
| Ingredients | Amount per 100 ml |
| Compound (1) | 100 mg |
| Glycerin | 2497 mg |
| Benzalkonium chloride | 10 mg |
| 1N hydrochloric acid | appropriate amount |
| 0.01N sodium hydroxide | appropriate amount |
| Sterile distilled water | appropriate amount |
| pH 7.0 | |

EXAMPLE 3

| Formulation 3: | |
|---|---|
| Ingredients | Amount per 100 ml |
| Compound (1) | 10 mg |
| Glycerin | 2545 mg |
| Benzalkonium chloride | 10 mg |
| 0.1N hydrochloric acid | appropriate amount |
| Sterile distilled water | appropriate amount |
| pH 7.0 | |

Production

Compound (1) was dissolved in 90 ml of sterile distilled water, and, to this solution, glycerin, benzalkonium chloride and 0.1N hydrochloric acid were dissolved, and to the mixture was added sterile distilled water to make 100 ml.

EXAMPLE 4

Additional eye drop (Formulation 4) was prepared according to the same procedure as described in Example 3.

| Formulation 4: | |
|---|---|
| Ingredients | Amount per 100 ml |
| Compound (1) | 1 mg |
| Glycerin | 2550 mg |
| Benzalkonium chloride | 10 mg |
| 0.1N hydrochloric acid | appropriate amount |
| Sterile distilled water | appropriate amount |
| pH 7.0 | |

EXAMPLE 5

| Formulation 5: | |
|---|---|
| Ingredients | Amount per 100 ml |
| Compound (1) | 100 mg |
| Boric acid | 1187 mg |
| Borax | 73 mg |
| NaCl | 269 mg |
| Benzalkonium chloride | 10 mg |
| Sterile distilled water | appropriate amount |
| pH 7.0 | |

Production

Compound (1), boric acid and borax were dissolved in 90 ml of sterile distilled water, and, to this solution, NaCl and benzalkonium chloride were dissolved, and to the resultant mixture was added sterile distilled water to make 100 ml.

EXAMPLE 6

| Formulation 6: | |
|---|---|
| Ingredients | Amount per 100 ml |
| Compound (1) | 100 mg |
| Potassium dihydrogen phosphate | 360 mg |
| Disodium hydrogen phosphate | 571 mg |
| NaCl | 439 mg |
| Benzethonium chloride | 10 mg |
| Sterile distilled water pH 7.0 | appropriate amount |

Production

Compound (1), potassium dihydrogen phosphate and disodium hydrogen phosphate were dissolved in 90 ml of sterile distilled water, and, to this solution, NaCl and benzethonium chloride were dissolved and added with sterile distilled water to make 100 ml.

Experiment 1: Main pharmacodynamics and pharmacology (ocular hypotensive effect)

The ocular hypotensive effect of the eye drops of this invention was investigated in rabbits. The same experiment was also conducted using a representative β-adrenergic blocking agent, and its ocular hypotensive effect was compared with that of eye drops of this invention.

Methods: According to the formulations described in Examples 1-4, eye drops containing 0.5%, 0.1%, 0.01% and 0.001% of the compound (1) were prepared. As a negative control, an eye drop not containing compound (1) was used. The positive control was a commercially available eye drop containing timolol maleate (0.5% equivalent of free base) as an active ingredient.

Male Japanese White rabbits (body weight: ca. 2 kg) with normal intraocular pressure were used in the experiment. Each of the test solutions (eye drops described in Examples 1-4) (50 µl) was instilled into one eye of each rabbit, and the control solution (eye drop of negative control mentioned below) (50 µl) into the fellow eye which served as a control. For each solution, four rabbits were used. After anesthesia of the corneal surface by instillating 5 µl of 0.4% oxybuprocaine hydrochloride, the intraocular pressure was measured using an applanation pneumatonogrpah (Alcon) before and after the instillation of the test solution and control solution. Measurement of intraocular pressure after the instillation was conducted with one-hour intervals until six hours post-instillation.

| Negative Control | |
|---|---|
| Ingredients | Amount per 100 ml |
| Glycerin | 2551 mg |
| Benzalkonium hydrochloride | 10 mg |
| 0.1N hydrochloric acid | appropriate amount |
| Sterile distilled water pH 7.0 | appropriate amount |

Production

Benzalkonium chloride and 0.1N hydrochloric acid were dissolved in 90 ml of sterile distilled water, and to the solution was added sterile distilled water to make 100 ml.

Results

The results of the above test involving the eye drops of the present invention are presented in FIG. 1, wherein difference in IOP between the control and the test eyes are shown. Table 1 compares the test results obtained with a commercial eye drop containing timolol maleate as an active ingredient with those obtained with the eye drops of the present invention. The eye drop containing 0.5% of compound (1) produced the maximal IOP reduction one hour post-instillation, with an average difference from the control eye drop of −2.8 mmHg, and this ocular hypotensive effect was retained even six hours post-instillation. Where the eye drop containing 0.1% of compound (1) was used, the IOP in the test eye was lower than that in the control eye, and average reduction of 2.3 mmHg was obtained one hour post-instillation. The eye drops of 0.01% and 0.001% concentration lowered the IOP in a dose-dependent manner.

On the other hand, the commercial eye drop containing timolol maleate as an active ingredient lowered the IOP, with a difference from the control eye of −0.8 mmHg both one and two hours post-instillation. At the same concentration (0.5%), the eye drop of the invention produced greater IOP reductions than the commercial eye drop, with average differences from the control eye of −2.8 mmHg and −1.7 mmHg at one and two hours post-instillation, respectively. It should be noted that the eye drop of the invention which contains only 0.1% of the compound (1) caused greater IOP reduction than the commercially available timolol maleate eye drop. These results shows the excellent ocular hypotensive effect of the eye drops of the invention which is superior to that of the typical commercial eye drop containing β-adrenoceptor blocker.

TABLE 1

| | Difference in IOP between the control and test eyes (mmHg) | | | | |
|---|---|---|---|---|---|
| drug | Concentration of free base (%) | 1 hr | 2 hr | 4 hr | 6 hr |
| Compound (1) | 0.5 | −2.75 | −1.68 | −1.00 | −0.56 |
| Compound (1) | 0.1 | −2.31 | −1.12 | −0.43 | 0.00 |
| Compound (1) | 0.01 | −1.18 | −0.62 | −0.18 | −0.12 |
| Compound (1) | 0.001 | −0.37 | −0.31 | 0.13 | 0.13 |
| Timolol maleate | 0.5 | −0.80 | −0.80 | −0.25 | −0.10 |

Experiment 2: Eye Irritation Test

The eye irritating effect of the eye drop of the present invention was investigated in rabbits. According to the descriptions in Experiment 1, eye drops containing different concentrations of compound (1) as an active ingredient were prepared, and their eye irritating effects were evaluated by modified Draize test (Gendaino Rinsho (Modern Clinics) 4: 277, 1970).

Methods

Male Japanese White rabbits (body weight: ca. 2 kg) were used in the experiment. The test solutions (eye drops described in Examples 1-3) (100 µl) was instilled into one eye of an animal eight times with 15-minutes intervals, and the control solution (eye drop described in Negative Control) into the fellow eye in the same manner. The degree of ocular irritation was scored according to the modified Draize method.

Results

The ocular irritation scores when 0.5% eye drop of the present invention was used are presented in FIG. 2. The irritation was examined before and after instillation, i.e., one, three, six and 24 hours post-instillation. No significant difference was observed in the Draize irritation scores between the test and control eyes. In the eyes treated with the 0.1% and 0.01% eye drops of the invention, the Draize irritation scores were not significantly different from those of the control eye. Thus, the experiment results demonstrate that the eye drops of the present invention give negligible irritation to rabbit eyes.

The pharmaceutical composition of the present invention shows an excellent ocular hypotensive effect and a minimal eye-irritating effect, and these advantages promise that the composition of the present invention is highly useful in the treatment of ocular hypertension and glaucoma.

What is claimed is:

1. A method of reducing intraocular pressure which comprises administering an effective amount of the compound of the formula (1):

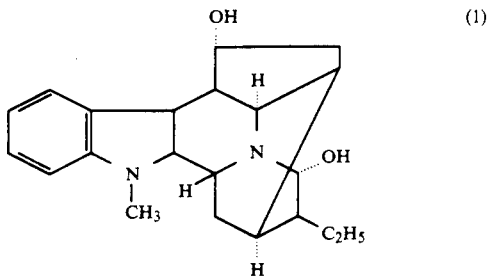

or a pharmaceutically acceptable salt thereof to patients suffering from elevated intraocular pressure.

2. The method as claimed in claim 1, wherein the compound (1) is topically administered.

* * * * *